United States Patent
Ertl et al.

(10) Patent No.: US 6,399,745 B1
(45) Date of Patent: Jun. 4, 2002

(54) USE OF LEPTIN ANTAGONISTS FOR TREATING INSULIN RESISTANCE IN TYPE II DIABETES

(75) Inventors: Johann Ertl, Bremthal; Gerald Preibisch, Kelkheim; Günter Müller, Sulzbach, all of (DE)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 09/147,805

(22) PCT Filed: Sep. 15, 1997

(86) PCT No.: PCT/EP97/05035

§ 371 (c)(1),
(2), (4) Date: Apr. 14, 1999

(87) PCT Pub. No.: WO98/12224

PCT Pub. Date: Mar. 26, 1998

(30) Foreign Application Priority Data

Sep. 20, 1996 (DE) .......................................... 196 38 487

(51) Int. Cl.[7] .................................................. C07K 1/00
(52) U.S. Cl. .......................................... 530/350; 514/2
(58) Field of Search ............................. 514/2, 12, 909; 530/300, 324, 350, 395

(56) References Cited

U.S. PATENT DOCUMENTS

| | | | | |
|---|---|---|---|---|
| 5,521,283 A | * | 5/1996 | DiMarchi et al. | 514/12 |
| 5,525,705 A | * | 6/1996 | DiMarchi et al. | 530/324 |
| 5,563,243 A | * | 10/1996 | DiMarchi et al. | 530/324 |
| 5,569,743 A | * | 10/1996 | DiMarchi et al. | 530/324 |
| 5,574,133 A | * | 11/1996 | DiMarchi et al. | 530/324 |
| 5,756,461 A | * | 5/1998 | Stephens | 514/12 |
| 5,922,678 A | * | 7/1999 | Stephens | 514/12 |
| 6,001,968 A | * | 12/1999 | Friedman et al. | 530/350 |
| 6,048,837 A | * | 4/2000 | Friedman et al. | 514/2 |

FOREIGN PATENT DOCUMENTS

| WO | WO 96 05309 | 2/1996 |
|---|---|---|
| WO | WO 97 26335 | 7/1997 |

OTHER PUBLICATIONS

Meinders et al, *Netherlands Journal of Medicine* V 49(6) Dec. 1996, (abstract.*

Kieffer, T., et al., "Leptin Receptors Expressed on Pancreatic β–Cells," Biochemical and Biophysical Research Communications, vol. 224, No. 2, pp. 522–527 (1996).

* cited by examiner

*Primary Examiner*—Lorraine Spector
(74) *Attorney, Agent, or Firm*—Heller Ehrman White and McAuliffe

(57) ABSTRACT

The invention relates to pharmaceutical agents containing leptin antagonists for treating Type II diabetes. One leptin antagonist is based on a murine leptin fragment and comprises amino acids 116 to 167 or 116 to 166. Methods of treating Type II diabetes are also disclosed.

2 Claims, 3 Drawing Sheets

FIG. 1

Human leptin (SEQ ID NO: 4)

```
1-Met His Trp Gly Thr Leu Cys Gly Phe Leu Trp Leu Trp Pro Tyr
  Leu Phe Tyr Val Gln Ala Val Pro Ile Gln Lys Val Gln Asp Asp
  Thr Lys Thr Leu Ile Lys Thr Ile Val Thr Arg Ile Asn Asp Ile
  Ser His Thr Gln Ser Val Ser Ser Lys Gln Lys Val Thr Gly Leu
  Asp Phe Ile Pro Gly Leu His Pro Ile Leu Thr Leu Ser Lys Met
  Asp Gln Thr Leu Ala Val Tyr Gln Gln Ile Leu Thr Ser Met Pro
  Ser Arg Asn Val Ile Gln Ile Ser Asn Asp Leu Glu Asn Leu Arg
  Asp Leu Leu His Val Leu Ala Phe Ser Lys Ser Cys His Leu Pro
  Trp Ala Ser Gly Leu Glu Thr Leu Asp Ser Leu Gly Gly Val Leu
  Glu Ala Ser Gly Tyr Ser Thr Glu Val Val Ala Leu Ser Arg Leu
  Gln Gly Ser Leu Gln Asp Met Leu Trp Gln Leu Asp Leu Ser Pro
  Gly Cys-167
```

FIG. 2

Murine leptin (SEQ ID NO: 5)

```
1-Met Cys Trp Arg Pro Leu Cys Arg Phe Leu Trp Leu Trp Ser Tyr
  Leu Ser Tyr Val Gln Ala Val Pro Ile Gln Lys Val Gln Asp Asp
  Thr Lys Thr Leu Ile Lys Thr Ile Val Thr Arg Ile Asn Asp Ile
  Ser His Thr Gln Ser Val Ser Ala Lys Gln Arg Val Thr Gly Leu
  Asp Phe Ile Pro Gly Leu His Pro Ile Leu Ser Leu Ser Lys Met
  Asp Gln Thr Leu Ala Val Tyr Gln Gln Val Leu Thr Ser Leu Pro
  Ser Gln Asn Val Leu Gln Ile Ala Asn Asp Leu Glu Asn Leu Arg
  Asp Leu Leu His Leu Leu Ala Phe Ser Lys Ser Cys Ser Leu Pro
  Gln Thr Ser Gly Leu Gln Lys Pro Glu Ser Leu Asp Gly Val Leu
  Glu Ala Ser Leu Tyr Ser Thr Glu Val Val Ala Leu Ser Arg Leu
  Gln Gly Ser Leu Gln Asp Ile Leu Gln Gln Leu Asp Val Ser Pro
  Glu Cys-167
```

FIG. 3

Fragment 116-167 from murine leptin (SEQ ID NO: 6)

1-Ser Cys Ser Leu Pro Gln Thr Ser Gly Leu Gln Lys Pro Glu Ser
  Leu Asp Gly Val Leu Glu Ala Ser Leu Tyr Ser Thr Glu Val Val
  Ala Leu Ser Arg Leu Gln Gly Ser Leu Gln Asp Ile Leu Gln Gln
  Leu Asp Val Ser Pro Glu Cys-167

The two cysteines present in the sequences shown in Tables 4 to 6 are linked by a disulfide bridge.

USE OF LEPTIN ANTAGONISTS FOR TREATING INSULIN RESISTANCE IN TYPE II DIABETES

BACKGROUND OF THE INVENTION

The present invention relates to the use of leptin antagonists for treating insulin resistance in Type II diabetes and to a pharmaceutical for treating such resistance.

Diabetes is one of the most frequently occurring metabolic diseases in industrialized countries. There are some 110 million diabetics world-wide; while approx. 10 million of these are Type I diabetics, the overwhelming majority (approx. 100 million) are Type II diabetics. The disease is caused by faulty regulation of glucose metabolism. In Type I diabetes, failure of the β cells in the pancreas results in insulin no longer being formed. This lack of insulin leads to an increase in blood glucose and, if not treated by supplying insulin, to ketoacidosis, diabetic coma and death of the patient. In Type II diabetics, the causal relationships are different and are characterized by the initial development of insulin resistance, i.e. diminution in the ability of the cells to respond adequately to insulin. Excessive weight and lack of physical activity, in particular, are regarded as being responsible for inducing insulin resistance. The latter condition is not noticed initially since it is offset by an increased secretion of insulin. However, the continuing insulin resistance leads, in a process extending over many years, to failure of the endogenous compensation mechanism and consequent development of Type II diabetes. While diet and physical activity can delay this sequence of events, they are frequently unable to prevent manifestation of the disease. Medicinal intervention is then required in order to control the blood glucose adequately.

It is of crucial importance for the long-term success of the therapy that the blood glucose be maintained as narrowly as possible within the physiological range. It is the current view that glucose levels which have been elevated for decades, as are found in poorly controlled diabetics (both Type I and Type II diabetics), make an important contribution to late complications in diabetes. These late complications constitute, in particular, blood vessel damage which leads to kidney diseases, loss of sight and cardiovascular diseases. This so-called late damage is an important factor contributing to mortality in diabetics.

In 1994, a new hormone, leptin, was described which is formed in fat cells and which is lacking in genetically overweight mice (ob/ob mice) (Zhang, Y., Proenca, R., Maffei, M., Barone, M., Leopold, L., and Friedman, J. M. (1994). Positional cloning of the mouse obese gene and its human homologue. Nature 372, 425–432.). Human leptin and murine leptin are to a large extent identical. Injecting ob/ob mice with recombinantly prepared leptin leads to a reduction in nutrient intake and to a decrease in weight (Pelleymounter, M. A., Cullen, M. J., Baker, M. B., Hecht, R., Winters, D., Boone, T., and Collins, F. (1995). Effects of the obese gene product on body weight regulation in ob/ob mice. Science 269, 540–543.). There has so far been no indication that mutations in the ob gene might be responsible for the frequent occurrence of obesity in humans (approx. 30% of the population is markedly overweight in the USA). Systematic investigations have demonstrated that serum levels of leptin are increased in obese humans as they are in various animal models of obesity (Dagogo-Jack, S., Fanelli, C., Paramore,: D., Brothers, J., and Landt, M. (1996). Plasma leptin and insulin relationships in obese and non-obese humans. Diabetes 45, 695–698; Considine, R. V., Sinha, M. K., Heiman, M. L., Kriauciunas, A., Stephens, T. W., Nyce, M. R., Ohannesian, J. P., Marco, C. C., McKee, L. J., Bauer, T. L., and Caro, J. F. (1996). Serum immunoreactive leptin concentrations in normal-weight and obese humans. N. Engl. J. Med. 334, 292–295.). For this reason, it is assumed that leptin is a feedback signal which informs the brain of the quantity of energy which is stored in the fat tissue. According to this assumption, it is then the function of the brain to decrease feed intake by inhibiting appetite, on the one hand, and to stimulate basal metabolism on the other. In human obesity, this regulatory circuit appears to be interrupted.

In addition to this, it is assumed that leptin also acts directly on tissues outside the brain.

Three studies relating to the direct effect of leptin on isolated cells have so far been published:

Kroder et al. (Kroder, G., Kellerer, M., and Häring, H. (1996) Exp. Crin. Endocrin. Diabetes 104 Suppl. 2, 66 (Abstract)) made the assumption that leptin establishes a connection between insulin resistance and obesity and report that leptin decreases insulin-induced phosphorylation of the insulin receptor and of insulin receptor substrate 1 (IRS-1) in rat 1 fibroblasts which are overexpressing the human insulin receptor. The extent to which leptin also exerts an influence on the end points of the insulin effect, for example stimulation of glucose transport or glycogen synthase, was not investigated or discussed.

It has been demonstrated that sensitivity to lipogenic hormones (dexamethasone and insulin) is decreased in transformed 30A5 preadipocytes which are overexpressing leptin (Bai, Y. L., Zhang, S. Y., Kim, K. S., Lee, J. K., and Kim, K. H. (1996) J. Biol. Chem. 271, 13939–13942). Fatty acid synthesis and the synthesis of neutral lipids were decreased by leptin overexpression even in the non-stimulated state. While control cells exhibited a marked increase in the rate of lipid synthesis after the cells had been treated With dexamethasone or insulin, or a combination of the two hormones, cells which were overexpressing leptin were hardly stimulated at all under these circumstances. In addition to this, an investigation was also undertaken of the inhibition of glycerophosphate dehydrogenase activity and of acetyl CoA carboxylase expression which occurs after treating the cells with a combination of dexamethasone and insulin. It was found that it was not possible to stimulate leptin-expressing cells. The effects which were observed indicate that leptin suppresses lipid metabolism in a general manner. There is no mention of any possible connection between obesity and insulin resistance.

In another model system, i.e. $C_2C_{12}$ mouse myotubes, it was found that leptin exhibits insulin-like effects (Berti, L., Kellerer, M., and Häring, H. (1996) Diabetologia 39 Suppl. 1, A59 (Abstract)). This study reports that both glucose transport and glycogen synthesis are stimulated by leptin. These findings conflict with those reported by the other authors and the results which are presented here. They possibly involve an effect which is specific for this cell type.

In our investigations into the effect of leptin on isolated rat adipocytes, a model system for fat tissue, it has now been found, surprisingly, that the insulin sensitivity of important metabolic pathways of the fat cell such as stimulation of lipogenesis, of glucose transport and of glycogenesis, is drastically reduced (Example 4) whereas the basal values remain unaffected. The same applies to the inhibition of isoproterenol-stimulated lipolysis. Glucose transport in isolated rat adipocytes is stimulated approximately 14-fold by adding insulin (10 nM). This capacity to be stimulated is reduced in a dose-dependent manner by preincubating with leptin at different concentrations for 15 hours. Leptin desensitizes the cells, i.e. an insulin resistance is produced. Dose/effect curves for insulin at different leptin concentrations (Example 5) demonstrate that the concentrations at which effects can already be detected in vitro, both as regards insulin (0.1–0.2 nM) and as regards leptin (0.5–1 nM), are within the physiological range (Dagogo-Jack et al., 1996; Considine et al., 1996). Higher leptin levels (2–4 nM) (Dagogo-Jack et al., 1996; Considine et al., 1996), are found in obese humans, ,so that it is possible that the insulin effect is more strongly impaired in these subjects. The conclusion therefore suggests itself that chronically elevated leptin, as can be seen in obese subjects, leads to insulin resistance. As already explained above, insulin resistance is an important factor in the pathogenesis of Type II diabetes.

It is therefore an object of the invention to provide novel leptin antagonists that may be formulated in pharmaceutical compositions. It is another object of the invention to provide methods of treating Type II diabetes and other insulin-related disorders.

The invention consequently relates to the use of leptin antagonists, in particular those which are derived from leptin itself, for preparing a pharmaceutical for use in Type II diabetes. The leptin antagonists for this use are described in more detail below.

SUMMARY OF THE INVENTION

According to a first object of the invention, pharmaceutical compositions are provided which comprise an antagonist of leptin. According to this same object, pharmaceutical compositions are disclosed which comprise leptin antagonists which are derived from leptin. Further according to this object, pharmaceutical compositions are revealed which comprise a leptin antagonist that is a soluble leptin receptor, or a derivative thereof.

According to a second object of the invention, methods are provided which utilize the inventive pharmaceutical compositions in the treatment of Type II diabetes. Also according to this object, methods are provided for restoring or amplifying the physiological effect of insulin.

BRIEF DESCRIPTION OF THE DRAWINGS

FIG. 1 is the amino acid sequence of human leptin (SEQ ID NO: 4). The two cysteins are linked by a disulfide bridge.

FIG. 2 is the amino acid sequence of murine leptin (SEQ ID NO: 5). The two cysteins are linked by a disulfide bridge.

FIG. 3 is the amino acid sequence of fragment 116–167 of murine leptin SEQ ID NO: 6). The two cysteins are linked by a disulfide bridge.

DETAILED DESCRIPTION OF THE INVENTION

The invention which is presented here is directed towards compositions and methods for reducing, or completely eliminating, insulin resistance by inhibiting the effect of leptin. For this purpose, use can be made of peptides which act as leptin antagonists and which lead, in isolated fat cells in vitro, to abolition of leptin-induced insulin resistance. These peptides are consequently suitable for the therapy of insulin resistance, preferably in obese patients.

Leptin Antagonists

Leptin antagonists according to the invention specifically include peptide antagonists. The said peptides are derived from leptin fragments and may be obtained, for example, by chemically or enzymically cleaving intact leptin (e.g. with lysyl endopeptidase, trypsin, endo-Arg C or cyanogen bromide) or be prepared by being expressed, directly or as a fusion protein, in microorganisms. In connection with preparing the peptides in microorganisms, there is no compulsion to rely on the presence of natural cleavage sites when selecting the fragments which are to be expressed. Human and animal leptin, for example rat, mouse, pig or humanoid ape leptin, are suitable for deriving the peptides.

One suitable exemplary peptide extends from amino acid 116 to amino acid 167 or from amino acid 116 to amino acid 166 (FIG. 3, SEQ ID NO: 6) in accordance with the sequence which has been published in Zhang et al., (1994) (Examples 3 and 6). In Example 6, adipocytes were incubated for approx. 15 hours in the presence of 10 nM leptin and different concentrations of the antagonistic 116–167 leptin fragment. The cells were then stimulated with 5 nM insulin. In this experiment, it was found that increasing quantitites of the antagonist lead to restoration of the capacity to be stimulated by inulin and no resistance develops in the presence of high concentrations of the leptin antagonist. Thus, using these and similar assays, one skilled in the art readily may ascertain the antagonistic properties of any leptin antagonist that would be useful according to the present invention.

In addition to this, analogues of the antagonistic leptin fragments can also be used in which one or more amino acids is/are replaced or deleted. Preferable replacements are conservative amino acid substitutions. Such conservative substitutions include charged-charged, polar-polar and hydrophobic-hydrophobic amino acid substitutions. For example, one or more aspartate residues can be replaced by glutamate residues and/or vice versa and/or one or more leucine residues can be replaced by isoleucine residues and/or vice versa. Other substitutions and deletions may rationally be made based on steric and structural considerations, such as amino acid size and propensity for helix making or breaking.

Molecular biological and biotechnological methods can be used to alter and optimize the antagonistic properties of the said peptides in a specific manner. In addition to this, the peptides can be modified chemically, for example by means of acetylation, carbamoylation, formylation, biotinylation, acylation, or derivatization with polyethylene glycol or hydrophilic polymers, in order to increase their stability or modulate their plasma half-life and pharmacokinetics.

Antibodies against leptin, in particular their leptin-binding domains, are also suitable as leptin antagonists for the said purpose. In addition to this, soluble leptin receptors and/or leptin receptor fragments, and fusions thereof with other proteins (e.g. the IgG Fc region), are also suitable. Like the peptide antagonists, any leptin antagonist which is a protein may be altered by molecular biological means. Similarly, these antagonists may be prepared by being expressed, directly or as a fusion protein, in microorganisms or any number of standard expression systems.

Pharmaceutical Compositions

The invention furthermore relates to a pharmaceutical which comprises the leptin antagonists which are described in this patent application.

The pharmaceuticals can be used, for example, in the form of pharmaceutical preparations which can be administered orally, for example in the form of tablets, coated tablets, hard or soft gelatin capsules, solutions, emulsions or suspensions. They can also be administered rectally, for example in the form of suppositories, or parenterally, for example in the form of injection solutions. The pharmaceuticals can also be administered by way of the mucous membranes of the nose, of the mouth or of the lung. In order to produce pharmaceutical preparations, these compounds can be worked into therapeutically inert, organic and inorganic excipients. Lactose, corn starch or derivatives thereof, talc and stearic acid or salts thereof are examples of such excipients for tablets, coated tablets and hard gelatin capsules. Water, polyols, sucrose, invert sugar and glucose are suitable excipients for preparing solutions. Water, alcohols, polyols, glycerol and vegetable oils are suitable excipients for injection solutions. Vegetable and hardened oils, waxes, fats and semi-liquid polyols are suitable excipients for suppositories. The pharmaceutical preparations can also comprise preservatives, solvents, stabilizers, wetting agents, emulsifiers, sweeteners, dyes, flavorants, salts for altering the osmotic pressure, buffers, coating agents, antioxidants and, where appropriate, other therapeutic active compounds.

Oral administration and injections are preferred. For injection, the novel leptin antagonists are formulated in a liquid solution, preferably in a physiologically acceptable buffer such as Hank's solution or Ringer's solution. However, the novel leptin antagonists can also be formulated in solid form and be dissolved or suspended prior to use.

Typical formulations contain a therapeutically beneficial amount of a leptin antagonist. A therapeutically beneficial amount may be the same as a therapeutically effective amount, as discussed below. Additionally, a therapeutically beneficial amount may be a unit dose, which either alone or in multiples may be used to provide a therapeutically effective amount of leptin antagonist. Thus, a therapeutically beneficial amount will rely, inter alia, on the nature of the disorder being treated.

Methods of Treatment

The methods of the invention are useful in treating any dirsorder in which the action of leptin is implicated. In view of the present dislcosure and the observation that leptin inhibits some of the physiological activities of insulin, the inventive methods are particularly useful in the treatment of disorders involving perturbations of insulin activity, and especially Type II diabetes. Such perturbations in insulin activity include alterations in lipogenesis, glucose transport glycogenesis and lipolysis. Accordingly, the inventive methods include methods for treating Type II diabetes and methods for restoring or amplifying the physiological effects of insulin.

A typical method entails administering to a patient in need of treatment a therapeutically effective amount of a leptin antagonist. A patient will be in need of treatment when suffering from a disorder in which the action of leptin is implicated. Treatment is especially indicated when a patient is suffering from Type II diabetes. Treatment is also indicated when a patient is suffering from a disorder characterized by a perturbation in insulin activity, such as alterations in lipogenesis, glucose transport, glycogenesis and lipolysis. In disorders where such a perturbation is implicated, methods for restoring or amplifying the physiological effect of insulin are useful.

A therapeutically effective amount will depend, for example, on the nature of the disorder being treated, the route of administration, the particular characteristics of the antagonist chosen, and especially the judgement of the attending clinician. A therapeutically effective amount generally is an amount sufficient to effect treatment of the disease targeted or to accomplish the stated goal of the method, for example, restoring or amplifying the physiological effect of insulin. Ultimately the therapeutically effective amount will depend on the clinically determined efficacy and toxicity of each leptin antagonist. Such determinations are routinely made and well within the ordinary skill of the clinician.

The term "treating" in its various grammatical forms in relation to the present invention refers to preventing, curing, reversing, attenuating, alleviating, minimizing, suppressing or halting the deleterious effects of a disease state, disease progression, disease causative agent or other abnormal condition.

The doses which are preferred for systemic administration are from approx. 0.01 mg/kg to approximately 50 mg/kg of body weight and per day.

The invention is clarified below by means of the Tables and Examples without being restricted thereto.

EXAMPLES

Example 1

Cloning Murine Leptin

RNA isolation—Epididymal fat pads are removed from adult mice and shock-frozen in liquid nitrogen. 1 g of fat tissue is ground in a mortar under liquid nitrogen, after which 15 ml of a 5 M solution of guanidinium thiocyanate in 50 mM Tris (pH 7.5), 10 mM EDTA and 0.1 M DTT are added and the whole is homogenized vigorously in order to obtain a fine dispersion. After the tissue particles have been completely dissipated, 10 g of solid CsCl are added and the mixture is stirred at room temperature. After adding 10 ml of $H_2O$, 9 ml of a 5.7 M solution of CsCl are overlaid with 25 ml of this solution in a centrifuge tube. After centrifuging for 15 hours in an SW28 rotor at 25,000 rpm (18° C.), the tube is deep-frozen in liquid nitrogen and the bottom quarter of the tube is cut off using a hot scalpel blade; the frozen contents are taken out and the RNA pellet is scraped off their bottom end. The RNA is dissolved and then precipitated with ethanol.

cDNA synthesis—In a mixture, 1 μg of total RNA from fat tissue and 1 μg of the specific primer oligonucleotide 5'-GAATGCAGAATAAATAAATA (SEQ ID NO.: 1; Zhang et al., 1994) are dissolved in 10 μl of $H_2O$ and are then heat-denatured and incubated at 65° C. for 5 min. After adding 0.5 μl of RNase inhibitor, in each case 5 nmol of dNTP and 0.5 μl of AMV reverse transcriptase (Boehringer Mannheim), the mixture is incubated at 42° C. for 1 h. After that the cDNA is made up to 200 μl with $H_2O$ and stored at −20° C.

PCR—3 μl of the specifically primed cDNA are amplified with 0.5 μg each of the two primers 5'-GAAAGAAGGATCCAGTGCCTATCCAGAAAGTCCA (SEQ ID NO.: 2) and 5'-GGAGAGAAGCTTGAGGGAGAGAAATGAATGATGG (SEQ ID NO.: 3; Zhang et al., 1994) and 2.5 U of Taq polymerase (Perkin Elmer) for 30 cycles in the reaction buffer recommended by the manufacturer (1.5 mM $MgCl_2$, 200 μM dNTPs in 100 μl). Each cycle comprises 1 min at 94° C., 1 min at 55° C. and 2 min 72° C. Ligation—The specifically amplified PCR product (583 bp) from a PCR preparation is cleaved, in each case at 37° C. for 2 h and under buffering conditions which accord with the manufacturer's instructions, with the restriction enzymes BamHI and HindIII (Boehringer Mannheim), after which the 564 bp fragment is purified by electrophoresis and isolated. It is incubated, at 30° C. for 2 h and in 20 µl, together with 0.1 µg of BamHI- and HindIII-cleaved vector pQE31 (Qiagen) and 20 U of T4 DNA ligase (New England Biolabs).

Cloning—5 µl of the ligation mixture are kept on ice for 30 min together with 100 µl of transformation-competent E. coli cells of the HB101 strain and the mixture is then swirled gently for 5 min in a water bath at 37° C. Following the addition of 0.9 ml of nutrient medium containing 10 mM $MgCl_2$, the mixture is shaken at 37° C. for 1 h. 100 µl volumes of this mixture are in each case plated onto ampicillin-containing (100 µg/ml) agar plates.

Identification of the clones—The clones which have grown overnight at 37° C. are inoculated into 2 ml-volume liquid cultures containing ampicillin, cultured to stationary phase and then centrifuged down. The cells are suspended in 0.1 ml of 25 mM Tris (pH 8), 50 mM glucose, 10 mM EDTA and lysozyme (2 mg/ml) and, after having been incubated at room temperature for 5 min, are lysed by adding 0.2 ml of 0.2 M NaOH, 1% SDS. The chromosomal DNA is precipitated by adding 150 µl of 3 M Na acetate/acetic acid (pH 5.2) and centrifuged down for 5 min at 4° C. (10,000 rpm in a Sigma 2MK). The plasmid DNA is precipitated with 2.5 volumes of ethanol, centrifuged down (see above) and, following an ethanol wash, taken up in 100 µl of $H_2O$; 10 µl of RNase solution (10 mg/ml) are then added.

The plasmid DNA is digested with restriction enzymes (BglI, XhoI+PvuII; Boehringer Mannheim) in accordance with the manufacturer's instructions, and the resulting DNA fragments are measured against marker DNA in an agarose gel following electrophoresis and staining with ethidium bromide. Clones which have the correct fragment pattern are examined in the same way using the restriction enzyme AflIII (New England Biolabs) for the presence of the glutamine 49 residue.

The identity of in each case one E. coli clone containing Gln49 (pQEob3-9) and one not containing Gln49 (pQEob3-4) was confirmed by means of DNA sequencing. The production of recombinant leptin containing the presequence (SEQ ID NO.: 7) MetArgGlySer(His)6ThrAspPro (from the vector pQE31) followed by amino acids 22 to 167 from murine leptin was checked in small cultures.

While both recombinant leptins (with and without Gln49) can be employed in the experiments which are described below, the examples specifically relate to leptin which contains Gln49 and which is obtained by expressing pQEob3-9.

Example 2

Preparation of Leptin

Disruption—The bacteria from a 10 l fermentation are centrifuged at 4800 rpm for 20 min. The sediment is frozen at −20° C. and subsequently suspended in lysis buffer (6 M guanidinium chloride, 0.1 M $NaH_2PO_4$, 10 mM Tris/HCl, pH 8) (5 ml of lysis buffer/g of sediment), after which the mixture is stirred at room temperature for one hour and then centrifuged at 4800 rpm for 30 min.

Ni-NTA chromatography—100 ml of Ni-NTA agarose FF (Qiagen, Hilden) are added to crude extract which contains approx. 800 mg of leptin and the whole is stirred at 4° C. overnight. The suspension is sucked through a glass column (ø5 cm) possessing a frit. The column, together with the Ni-NTA agarose which is contained in it, is washed with 300 ml of lysis buffer and then with 100 ml of lysis buffer containing 10 mM imidazole (5 ml/min). Fractional elution of the leptin then takes place by applying a linear gradient of 10 to 200 mM imidazole in lysis buffer (gradient volume: 300 ml at 5 ml/min). The fractions are analyzed by RP-HPLC and those which are of adequate purity and concentration are combined (=Ni-NTA eluate).

Folding—The Ni-NTA eluate is diluted with lysis buffer to a concentration of 1–3 mg/ml and adjusted to pH 9 with sodium hydroxide solution. After adding β-mercaptoethanol (from 4 to 6 mol of β-mercaptoethanol per mole of leptin), the mixture is incubated at room temperature for 2 hours in a sealed container. For reoxidation and refolding, the solution is poured into 9 time's the volume of folding buffer (0.1 M Tris/HCl, pH 9) and the whole is stirred at 16° C. for from 16 to 24 hours while admitting air. Any turbidity which appears is centrifuged off (4,000 rpm, 45 min).

Reversed phase HPLC—The folding mixture is adjusted to pH 3 with HCl and pumped onto a 2.5×30 cm RP column (PLRPS 300 Å, 10µ, Polymer Laboratories, Amherst, USA) at the rate of 20 ml/min. The column is subsequently washed with 300 ml of eluent A (0.1 % aqueous TFA). Leptin is eluted in 100 minutes (flow rate: 7 ml/min) by applying a gradient of from 25 to 50% eluent B (0.09% TFA in acetonitrile). The fractions are analyzed by means of analytical HPLC. Fractions of adequate purity and concentration are combined (RP pool). The pool is treated with 7 mmol of $Na_2HPO_4$/l and adjusted to pH 3 with NaOH, and the solvent is removed on a rotary evaporator. The aqueous leptin solution is then neutralized with NaOH (pH 7.4) and stored at 4° C. overnight. Any resulting turbidity is centrifuged off((4,000 rpm, 10 min).

Gel permeation chromatography—The neutralized and centrifuged leptin solution is concentrated to 10–15 mg/ml by ultrafiltration and then sterilized by filtration. From 50 to 75 mg are loaded onto a Superdex 75 column (2.6×60 cm, Pharmacia, Sweden). PBS (154 mM NaCl, 10 mM sodium phosphate, pH 7.4) is used as the elution buffer, at a flow rate of 3 ml/min. The leptin which has been purified in this way is then filtered once again through a 0.22 µm membrane and stored at −70° C.

Example 3

Preparation of the Antagonistic 116–167 Fragment 1 ml of 1 M Tris/HCl, pH 8, is added to 40 ml of a solution of leptin (1 mg/ml in PBS) and, after 160 µg of lysyl endopeptidase have been added, the leptin is digested at room temperature for 3 h. The mixture is adjusted to pH 3 and fractionated by RP-HPLC as described in Example 2. The 116–167 fragment is identified by electrospray mass spectrometry (5532 D), freed from solvent as described in Example 2, concentrated and purified by means of gel permeation chromatography.

Example 4

Isolation of Adipocytes

Adipocytes were prepared from the epididymal fat tissue of male Wistar rats (140–160 g, Hoechst AG breeding station, Kastengrund) by means of digesting with collagenase (Rodbell, 1964, J. Biol. Chem. 239, 375–380), washed twice with KRH (25 mM Hepes free acid, 25 mM Hepes sodium salt, 80 mM NaCl, 1 mM $MgSO_4$, 2 mM $CaCl_2$, 6 mM KCl, 1 mM sodium pyruvate, 0.5% BSA) and once with DMEM (Dulbecco's minimal essential medium), supplemented with 5.5 mM glucose, 20 mM Hepes (pH 7.4), 2% fetal calf serum, 1% BSA, 50 U of penicillin/ml, 10 mg of streptomycin/ml, by means of flotation (800×g, 1 min, in small plastic tubes), and finally diluted to a volume of 20 ml of DMEM/g wet weight of the fat tissue (cell titer: approximately $2.5 \times 10^5$ cells/ml).

Example 5

Primary Culture of the Adipocytes and Incubation with Leptin

The adipocytes were incubated, at 37° C. for 15–18 h under an atmosphere of 5% $CO_2$ and with gentle shaking, in supplemented (see above) DMEM in the presence of 100 nM phenylisopropyladenosine (4 ml of DMEM to 1 ml of cells, cell titer approximately $5 \times 10^4$ cell/ml, in 50 ml sterile polypropylene: tubes) and in the presence or absence of leptin. The adipocytes were subsequently washed three times with cold KRH and adjusted to a cell titer of approximately $3 \times 10^5$ cells/ml by adding 0.7 ml of glucose-free KRH to the cell layer which remained after the complete removal of the last washing solution. In order to determine the capacity of the adipocytes to be stimulated by insulin, and their sensitivity to insulin, following the primary culture, the washed adipocytes were incubated at 37° C. for 20 min in the absence or presence of human insulin (0.02–50 nM final concentration), and glucose transport or lipogenesis was then measured.

Example 6

Glucose Transport

Glucose transport was measured as the specific uptake of the non-metabolizable glucose analog 2-deoxyglucose (Muller and Wied, 1993, Diabetes 42, 1852–1867). 50 μl of the adipocyte suspension in KRH, which suspension had or had not been preincubated with insulin (see above), were incubated, at 25° C. for 5 min, with 50 μl of KRH which was supplemented with 2-deoxy-D-[2,6-$^3$H]glucose (0.5 μCi, 0.2 mM). The incubation mixtures were transferred to thin soft-plastic centrifuge tubes, each of which already contained 200 μl of dinonyl phthalate oil, and immediately centrifuged (2,000×g, 30 sec). Using special shears, the tubes were severed within the oil layer (in the vicinity of the upper edge) and the upper halves of the tubes, together with the cell layers which had in each case been floated onto the oil layer, were transferred to scintillation vials. After 10 ml of scintillation fluid (water-based) had been added, the radioactivity associated with the cells was measured. In order to correct for 2-deoxyglucose which had become enclosed in the cell interstices, or had diffused into the cells, in a non-specific manner, the radioactivity of cells which had been preincubated with cytochalasin B (20 μM) was subtracted from the total cell-associated radioactivity of each individual incubation mixture (Gliemann et al., 1972, Biochim. Biophys. Acta 286, 1–9).

Example 7

Lipogenesis

Lipogenesis was measured as the incorporation of D-glucose into toluene-extractable lipids (Moody et al., 1974, Horm. Metab. Res. 6, 12–16). 200 μl of the adipocyte suspension in KRH were incubated in scintillation vials, at 37° C. for 20 min, in 680 μl of KRH which was supplemented with 3.5 mM glucose and 20 μl of insulin solution. Lipogenesis was started by adding 100 μl of D-[3-$^3$H] glucose (25 μCi/ml KRH). After incubating at 37° C., and gently shaking under an atmosphere of 5% $CO_2$, for 90 min, 10 ml of scintillation fluid (toluene-based) were added and the radioactivity in the toluene phase was determined after shaking vigorously and subsequent phase separation (at least 4 h of incubation). The radioactivity of the lipids in the toluene phase was corrected for the radioactivity of an incubation mixture which contained the same quantity of [$^3$H]glucose but no cells.

Example 8

Inhibition by Leptin of Insulin-induced Glucose Transport and of Insulin-Induced Lipogenesis Isolated rat adipocytes were incubated for 15 h in primary culture in the presence or absence of increasing concentrations of leptin. The cells were then washed and tested for glucose transport and lipogenesis in the basal and insulin (10 nM)-stimulated states. The stimulation factor for insulin was calculated as the ratio between insulin-stimulated and basal activities. Each value represents the mean from two independent adipocyte cultures with activity being determined two or three times in each case.

TABLE 1

| Insulin concentration: 5 nM | | |
|---|---|---|
| Leptin Concentration [nM] | Glucose Transport* | Lipogenesis* |
| 0 | 13.4 | 3.9 |
| 0.3 | 13.4 | 3.9 |
| 1 | 11.75 | 3.2 |
| 3 | 7.4 | 2.15 |
| 10 | 3.5 | 1.5 |
| 30 | 2.35 | 1.15 |
| 100 | 1.5 | 1.05 |

*The factors are the quotients of the values following stimulation and the basal values.

The results are summarized in Table 1.

Example 9

Influence of Leptin on the Insulin Dose/Effect Curve

Isolated rat adipocytes were incubated for 16.5 h in primary culture in the presence or absence of increasing concentrations of leptin. The cells were then washed and tested for the stimulation of glucose transport by differing concentrations of insulin. Glucose transport activity is given as a "dpm value" of the 2deoxy-[$^3$H]glucose which is specifically associated with the cells. Each value represents the mean from two independent adipocyte cultures with the activity being determined four times in each case.

TABLE 2

| Measured parameter: glucose transport | | | | | | | | |
|---|---|---|---|---|---|---|---|---|
| | Leptin [nM] | | | | | | | |
| Insulin [nM] | 0 | 0.05 | 1 | 2 | 5 | 10 | 30 | 100 |
| 0 | 671 | 654 | 634 | 688 | 712 | 755 | 688 | 747 |
| 0.02 | 784 | 735 | 678 | 704 | 734 | 773 | 704 | 766 |
| 0.05 | 1285 | 1025 | 824 | 755 | 798 | 802 | 745 | 780 |

TABLE 2-continued

Measured parameter: glucose transport

| Insulin [nM] | Leptin [nM] | | | | | | | |
|---|---|---|---|---|---|---|---|---|
| | 0 | 0.05 | 1 | 2 | 5 | 10 | 30 | 100 |
| 0.1 | 2406 | 1674 | 1189 | 860 | 883 | 856 | 789 | 803 |
| 0.2 | 4762 | 3320 | 1587 | 1006 | 923 | 941 | 852 | 813 |
| 0.5 | 6976 | 5138 | 2180 | 1377 | 1167 | 1209 | 943 | 883 |
| 1 | 7981 | 6834 | 3904 | 1916 | 1583 | 1573 | 1183 | 896 |
| 2 | 8576 | 7942 | 5510 | 2680 | 2140 | 2061 | 1374 | 1034 |
| 5 | 8956 | 8794 | 6985 | 4323 | 2950 | 2476 | 1782 | 1205 |
| 10 | 9064 | 9134 | 8241 | 6107 | 3682 | 2710 | 1972 | 1451 |
| 50 | 9072 | 9189 | 8932 | 7032 | 4031 | 2967 | 2114 | 1723 |

The value given is in each case the uptake of $^3$H-labeled 2-deoxyglucose measured in dpm (disintegrations per minute).

The results are summarized in Table 2.

Example 10

The Antagonism of Fragment 116–167 to the Leptin Effect

Isolated rat adipocytes were incubated for 17.5 h in primary culture in the presence or absence of leptin (10 nM) and increasing concentrations of leptin fragment 116–167. The cells were then washed and tested for stimulation of glucose transport or lipogenesis by 5 nM insulin. The stimulation factor for insulin was calculated as the ratio between the insulin-stimulated activity and the basal activity. Each value represents the mean from two independent adipocyte cultures with activity being determined three times in each case.

TABLE 3

| | Leptin: 10 nM | |
|---|---|---|
| | Insulin: 5 nM | |
| Fragment Concentration [nM] | Glucose Transport* | Lipogenesis |
| 0 | 3.55 | 1.5 |
| 0.3 | 3.65 | 1.65 |
| 1 | 4.5 | 2.15 |
| 3 | 5.75 | 2.65 |
| 10 | 7.75 | 3.1 |
| 30 | 10.8 | 3.6 |
| 100 | 12.55 | 4 |
| 300 | 13.2 | 4 |
| Insulin only | 13.4 | 3.9 |

*The factors are the quotients of the values following stimulation and the basal values.

The results are summarized in Table 3.

FIG. 1: SEQ ID NO: 4

```
Human leptin
1-Met His Trp Gly Thr Leu Cys Gly Phe Leu Trp Leu Trp Pro Tyr

Leu Phe Tyr Val Gln Ala Val Pro Ile Gln Lys Val Gln Asp Asp

Thr Lys Thr Leu Ile Lys Thr Ile Val Thr Arg Ile Asn Asp Ile

Ser His Thr Gln Ser Val Ser Ser Lys Gln Lys Val Thr Gly Leu

Asp Phe Ile Pro Gly Leu His Pro Ile Leu Thr Leu Ser Lys Met

Asp Gln Thr Leu Ala Val Tyr Gln Gln Ile Leu Thr Ser Met Pro

Ser Arg Asn Val Ile Gln Ile Ser Asn Asp Leu Glu Asn Leu Arg

Asp Leu Leu His Val Leu Ala Phe Ser Lys Ser Cys His Leu Pro

Trp Ala Ser Gly Leu Glu Thr Leu Asp Ser Leu Gly Gly Val Leu

Glu Ala Ser Gly Tyr Ser Thr Glu Val Val Ala Leu Ser Arg Leu

Gln Gly Ser Leu Gln Asp Met Leu Trp Gln Leu Asp Leu Ser Pro

Gly Cys-167
```

FIG. 2: SEQ ID NO: 5

```
Murine leptin
1-Met Cys Trp Arg Pro Leu Cys Arg Phe Leu Trp Leu Trp Ser Tyr

Leu Ser Tyr Val Gln Ala Val Pro Ile Gln Lys Val Gln Asp Asp

Thr Lys Thr Leu Ile Lys Thr Ile Val Thr Arg Ile Asn Asp Ile

Ser His Thr Gln Ser Val Ser Ala Lys Gln Arg Val Thr Gly Leu

Asp Phe Ile Pro Gly Leu His Pro Ile Leu Ser Leu Ser Lys Met

Asp Gln Thr Leu Ala Val Tyr Gln Gln Val Leu Thr Ser Leu Pro
```

-continued

Ser Gln Asn Val Leu Gln Ile Ala Asn Asp Leu Glu Asn Leu Arg

Asp Leu Leu His Leu Leu Ala Phe Ser Lys Ser Cys Ser Leu Pro

Gln Thr Ser Gly Leu Gln Lys Pro Glu Ser Leu Asp Gly Val Leu

Glu Ala Ser Leu Tyr Ser Thr Glu Val Val Ala Leu Ser Arg Leu

Gln Gly Ser Leu Gln Asp Ile Leu Gln Gln Leu Asp Val Ser Pro

Glu Cys-167

FIG. 3: SEQ ID NO: 6

116-Ser Cys Ser Leu Pro Gln Thr Ser Gly Leu Gln
    Lys Pro Glu Ser Leu Asp Gly Val Leu Glu Ala
    Ser Leu Tyr Ser Thr Glu Val Val Ala Leu Ser
    Arg Leu Gln Gly Ser Leu Gln Asp Ile Leu Gln
    Gln Leu Asp Val Ser Pro Glu Cys-167

The two cysteines present in the sequences shown in Tables 4 to 6 are linked by a disulfide bridge.

---

What is claimed is:

1. A leptin antagonist which is a peptide having the amino acid sequence of SEQ ID NO. 6.

2. The leptin antagonist of claim 1, which in an in vitro assay, inhibits leptin from reducing insulin-induced glucose transport levels in adipocyte cells in culture.

* * * * *

SEQUENCE LISTING (1) GENERAL INFORMATION:

(iii) NUMBER OF SEQUENCES: 7

(2) INFORMATION FOR SEQ ID NO: 1:

(i) SEQUENCE CHARACTERISTICS:
    (A) LENGTH: 20 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO: 1:

GAATGCAGAA TAAATAAATA        20

(2) INFORMATION FOR SEQ ID NO: 2:

(i) SEQUENCE CHARACTERISTICS:
    (A) LENGTH: 34 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO: 2:

GAAAGAAGGA TCCAGTGCCT ATCCAGAAAG TCCA        34

(2) INFORMATION FOR SEQ ID NO: 3:

(i) SEQUENCE CHARACTERISTICS:
    (A) LENGTH: 34 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO: 3:

GGAGAGAAGC TTGAGGGAGA GAAATGAATG ATGG                                34

(2) INFORMATION FOR SEQ ID NO: 4:

(i) SEQUENCE CHARACTERISTICS:
        (A) LENGTH: 167 amino acids
        (B) TYPE: amino acid
        (C) STRANDEDNESS: <Unk nown>
        (D) TOPOLOGY: linear (ii) MOLECULE TYPE: peptide (xi) SEQUENCE DESCRIPTION: SEQ ID NO: 4:

Met His Trp Gly Thr Leu Cys Gly Phe Leu T rp Leu Trp Pro Tyr Le
1               5                   10                  15

Phe Tyr Val Gln Ala Val Pro Ile Gln Lys V al Gln Asp Asp Thr Ly
                20                  25                  30

Thr Leu Ile Lys Thr Ile Val Thr Arg Ile A sn Asp Ile Ser His Th
            35                  40                  45

Gln Ser Val Ser Lys Gln Lys Val Thr G ly Leu Asp Phe Ile Pr
    50                  55                  60

Gly Leu His Pro Ile Leu Thr Leu Ser Lys M et Asp Gln Thr Leu Al
65                  70                  75                  80

Val Tyr Gln Gln Ile Leu Thr Ser Met Pro S er Arg Asn Val Ile Gl
                85                  90                  95

Ile Ser Asn Asp Leu Glu Asn Leu Arg Asp L eu Leu His Val Leu Al
                100                 105                 110

Phe Ser Lys Ser Cys His Leu Pro Trp Ala S er Gly Leu Glu Thr Le
            115                 120                 125

Asp Ser Leu Gly Gly Val Leu Glu Ala Ser G ly Tyr Ser Thr Glu Va
    130                 135                 140

Val Ala Leu Ser Arg Leu Gln Gly Ser Leu G ln Asp Met Leu Trp Gl
145                 150                 155                 160

Leu Asp Leu Ser Pro Gly Cys
                165

(2) INFORMATION FOR SEQ ID NO: 5:

(i) SEQUENCE CHARACTERISTICS:
        (A) LENGTH: 167 amino acids
        (B) TYPE: amino acid
        (C) STRANDEDNESS: <Unk nown>
        (D) TOPOLOGY: linear (ii) MOLECULE TYPE: peptide (xi) SEQUENCE DESCRIPTION: SEQ ID NO: 5:

Met Cys Trp Arg Pro Leu Cys Arg Phe Leu T rp Leu Trp Ser Tyr Le
1               5                   10                  15

Ser Tyr Val Gln Ala Val Pro Ile Gln Lys V al Gln Asp Asp Thr Ly
                20                  25                  30

Thr Leu Ile Lys Thr Ile Val Thr Arg Ile A sn Asp Ile Ser His Th
            35                  40                  45

Gln Ser Val Ser Ala Lys Gln Arg Val Thr G ly Leu Asp Phe Ile Pr
    50                  55                  60

Gly Leu His Pro Ile Leu Ser Leu Ser Lys M et Asp Gln Thr Leu Al
65                  70                  75                  80

Val Tyr Gln Gln Val Leu Thr Ser Leu Pro S er Gln Asn Val Leu Gl
                85                  90                  95

```
Ile Ala Asn Asp Leu Glu Asn Leu Arg Asp Leu Leu His Leu Leu Al
            100                 105                 110
Phe Ser Lys Ser Cys Ser Leu Pro Gln Thr Ser Gly Leu Gln Lys Pr
            115                 120                 125
Glu Ser Leu Asp Gly Val Leu Glu Ala Ser Leu Tyr Ser Thr Glu Va
            130                 135                 140
Val Ala Leu Ser Arg Leu Gln Gly Ser Leu Gln Asp Ile Leu Gln Gl
145                 150                 155                 160
Leu Asp Val Ser Pro Glu Cys
                165

(2) INFORMATION FOR SEQ ID NO: 6:

(i) SEQUENCE CHARACTERISTICS:
        (A) LENGTH: 52 amino acids
        (B) TYPE: amino acid
        (C) STRANDEDNESS: <Unk nown>
        (D) TOPOLOGY: linear (ii) MOLECULE TYPE: peptide (xi) SEQUENCE DESCRIPTION: SEQ ID NO: 6:

Ser Cys Ser Leu Pro Gln Thr Ser Gly Leu Gln Lys Pro Glu Ser Le
1               5                   10                  15
Asp Gly Val Leu Glu Ala Ser Leu Tyr Ser Thr Glu Val Val Ala Le
            20                  25                  30
Ser Arg Leu Gln Gly Ser Leu Gln Asp Ile Leu Gln Gln Leu Asp Va
            35                  40                  45
Ser Pro Glu Cys
    50

(2) INFORMATION FOR SEQ ID NO: 7:

(i) SEQUENCE CHARACTERISTICS:
        (A) LENGTH: 13 amino acids
        (B) TYPE: amino acid
        (C) STRANDEDNESS: <Unk nown>
        (D) TOPOLOGY: linear (ii) MOLECULE TYPE: peptide (xi) SEQUENCE DESCRIPTION: SEQ ID NO: 7:

Met Arg Gly Ser His His His His His Thr Asp Pro
1               5                   10
```